United States Patent [19]
De Ruggieri et al.

[11] 4,005,079
[45] Jan. 25, 1977

[54] TETRAHYDROPYRANYL ETHERS OF ESTROGENS

[75] Inventors: Pietro De Ruggieri; Orazio Sighinolfi, both of Milan, Italy

[73] Assignee: Farmila Farmaceutici Milano S.p.A., Italy

[22] Filed: Nov. 19, 1975

[21] Appl. No.: 633,476

[30] Foreign Application Priority Data

Dec. 13, 1974 Italy .................................. 30574/74

[52] U.S. Cl. ...................................... 260/239.55 D
[51] Int. Cl.$^2$ .......................................... C07J 21/00
[58] Field of Search ........................... 260/239.55 D

[56] References Cited
UNITED STATES PATENTS

| | | | |
|---|---|---|---|
| 3,697,558 | 10/1972 | Back et al. | 260/239.55 D |
| 3,905,962 | 9/1975 | Marx et al. | 260/239.55 D |
| 3,951,958 | 4/1976 | Prezewowsky et al. | 260/239.55 D |

*Primary Examiner*—Elbert L. Roberts
*Attorney, Agent, or Firm*—Hill, Gross, Simpson, Van Santen, Steadman, Chiara & Simpson

[57] ABSTRACT

Tetrahydropyranyl ethers of estrogens have interesting properties in the cure of climateric and menopausal disturbances, with an excellent dissociation index between their selective effect on the vagina and their very small or zero effect on the endometrium.

5 Claims, No Drawings

TETRAHYDROPYRANYL ETHERS OF ESTROGENS

This invention provides, as new compounds, the estrogen derivatives of the formula

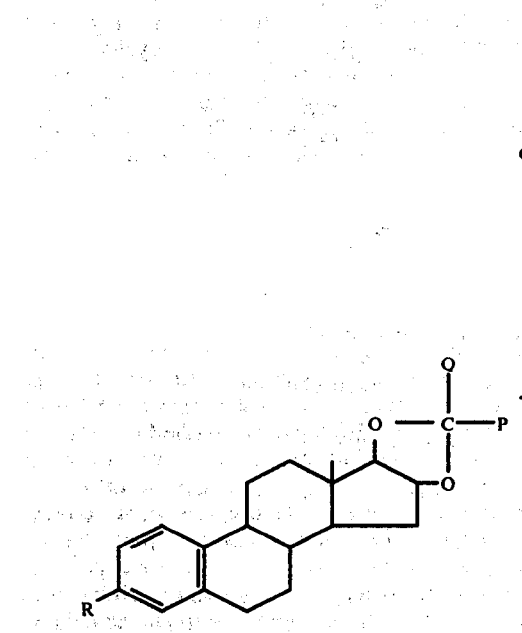

where R is 2'-tetrahydropyranyloxy or benzyloxy, P is hydrogen, lower alkyl, monocyclic cycloalkyl or monocyclic aryl, and Q is lower alkyl, monocyclic cycloalkyl, or monocyclic aryl.

It should be noted that the introduction of the tetrahydropyranyloxy radical comprising one asymmetrical carbon atom leads to two diastereoisomers R and S with a possible $\alpha$ and $\beta$ anomer configuration, the $\alpha$ (axial) configuration being the preferred, as it is stabilised by two ethereal dipoles of antiparallel position on the two oxygen atoms present.

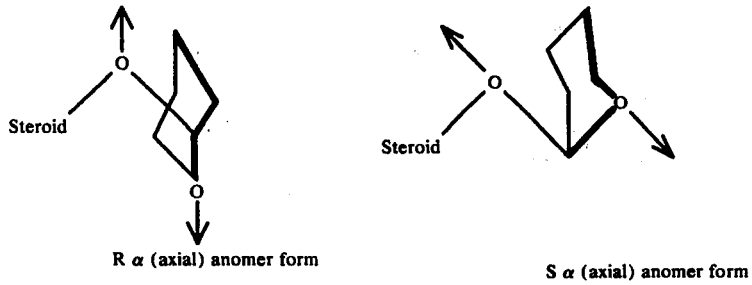

R $\alpha$ (axial) anomer form

S $\alpha$ (axial) anomer form

The present invention therefore relates both to the mixture R + S and to the two separate R and S diastereoisomers.

These compounds, derived from the estrogen series have favourable therapeutic properties in the cure of climateric and menopausal disturbances, with an excellent dissociation index between their selective effect on the vagina and their very small or zero effect on the endometrium; the administration of the compounds can be effected orally, in the form of capsule, tablets, dragees or by injection in oil solution, with daily dosages from 1 to 25 mg. for treatments continued for 3 weeks, followed by an interruption of one week, or for more extended cycles. Further, they have a marked activity even by topical way and can be employed as creams, ointments, vaginal taper and like.

The invention also provides a process for preparing said compounds, as shown in Equation 1 :

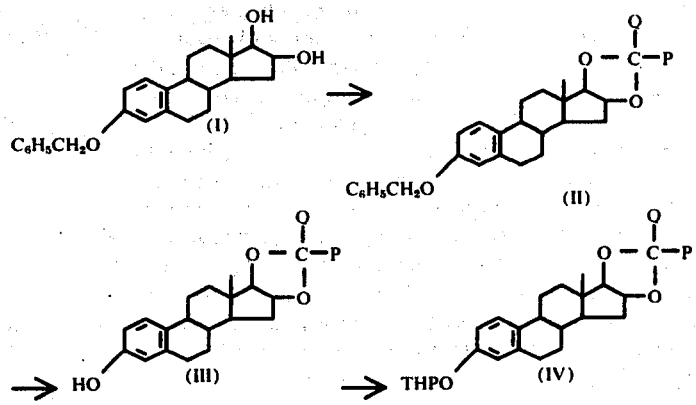

where P is hydrogen, lower alkyl, monocyclic cycloalkyl or monocyclic aryl, Q is lower alkyl, monocyclic cycloalkyl or monocyclic aryl, and THPO is 2'-tetrahydropyranyloxy.

On reaction with acetone or other ketones or aldehydes in the presence of perchloric acid, the cisdiol (I), prepared as described in Applicant's copending application U.S. Ser. No. 633,474 filed on the same day as the instant application, gave 3-benzyloxy-16$\beta$,17$\beta$-(iso)alkylidene-dioxy-estra-1,3,5(10)-trienes (II). These latter, when subjected to destructive hydrogenation (i.e. hydrogenalysis of the benzyl group) and then treated with 2,3-dihydropyran, finally gave 3-(2'-tetrahydropyranyloxy)-16$\beta$,17$\beta$-(iso) alkylidene-dioxyestra-1,3,5(10)-trienes (IV).

The following Example illustrate the present invention.

EXAMPLE 3-(2'-Tetrahydropyranyloxy)-16$\beta$,17$\beta$-isopropylidenedioxy-estra-1,3,5(10)-triene (IV, where P = CH$_3$).

A solution containing 14 parts of 3-benzyloxy-estra-1,3,5(10)-trien-16$\beta$,17$\beta$-diol (I) in 700 parts of acetone and 3 parts of 70% HClO$_4$ is left to stand overnight. The reaction mixture is added to water and neutralised with 1N NaOH.

The precipitate obtained, filtered off and dried, is dissolved in 250 parts of dioxane. Ten parts of carbon containing 5% of palladium are added; the mixture is shaken and made to absorb hydrogen at room temperature and pressure until no more is absorbed. After removing the catalyst by filtration, the solvent is evaporated to dryness under vacuum. The residue is dissolved in 300 parts of anhydrous benzene and treated with 0,4 parts of p-toluenesulphonic acid and 10 parts of 2,3-dihydropyran overnight at room temperature. The reaction mixture is washed with an aqueous solution of $NaHCO_3$ (10% w/v) and then with water to neutrality, and the aqueous phase is evaporated under vacuum to dryness. The residue, containing the mixture R + S of the 3-(2'-tetrahydropyranyloxy)-16β,17β-isopropylidendioxy-estra-1,3,5(10)-triene, is fractionally crystallized from diethyl ether, then from methanol, giving the pure diastereoisomers 3-(2'-R- -tetrahydropyranyloxy)-16β,17β-isopropylidenedioxy-estra-1,3,5(10)-triene (R-IV, where P = Q = $CH_3$), m.p. 122°–4° C, $[α]_D = -12°$ (chloroform), and 3-(2'-S-tetrahydropyranyloxy)-16β,17β-isopropylidenedioxy-estra-1,3,5(10)-triene (S-IV, where P=Q=$CH_3$), m.p. 108-10° C, $[α]_D = -115°$ (chloroform).

We claim:

1. Compound of the formula

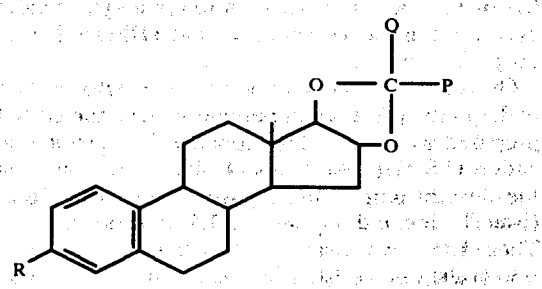

in which R is benzyloxy or 2'-tetrahydropyranyloxy; P is hydrogen, lower alkyl, monocyclic cycloalkyl or monocyclic aryl; Q is lower alkyl, monocyclic cycloalkyl or monocyclic aryl;

2. Process for preparing a compound of the formula

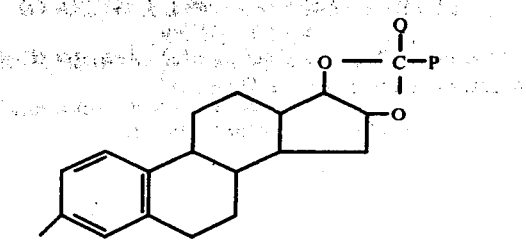

in which R is benzyloxy or 2'-tetrahydropyranyloxy; P is hydrogen, lower alkyl, monocyclic cycloalkyl or monocyclic aryl; Q is lower alkyl, monocyclic cycloalkyl or monocyclic aryl; which comprises reacting a corresponding 3-benzyloxy-16β,17β-dihydroxy compound with a ketone or aldehyde having the formula

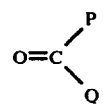

wherein P and Q are as above in the presence of an acid catalyst; subjecting the cyclic 3-benzyloxy-16β,17β-acetal thus obtained to hydrogenalysis of the benzyl group and finally etherifying the phenolic function thus liberated with 2,3-dihydropyran in the presence of an acid catalyst.

3. Process according to claim 2 in which the dihydroxy compound used as starting material is reacted with acetone, cyclohexanone, acetophenone, paraldehyde, or benzaldehyde, in the absence of solvent or in an organic solvent if the carbonyl compound is solid, in the presence of, as catalyst, perchloric, p-toluenesulphonic or hydrochloric acid; the hydrogenation is effected in ethanol alone or mixed with dioxane, tetrahydrofuran or ethyl acetate, in the presence of 2.5 to 10% Pd on carbon, and the etherification is effected in the presence of p-toluenesulphonic acid, $POCl_3$ or HCl in 2,3-dihydropyran, tetrahydrofuran, dioxane or benzene.

4. 3-Benzyloxy-16β,17β-isopropylidenedioxy estra-1,3,5(10)-triene.

5. 3-(2'-Tetrahydropyranyloxy)-16β,17β-isopropylidenedioxy-estra-1,3,5(10)-triene.

* * * * *